(12) United States Patent
Ohno et al.

(10) Patent No.: US 8,692,038 B2
(45) Date of Patent: Apr. 8, 2014

(54) FLUORINE-CONTAINING COMPOUND PURIFICATION METHOD

(75) Inventors: Hiromoto Ohno, Minato-ku (JP); Toshio Ohi, Minato-ku (JP); Katsutoshi Morinaka, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 13/504,335

(22) PCT Filed: Oct. 26, 2010

(86) PCT No.: PCT/JP2010/068912
§ 371 (c)(1),
(2), (4) Date: Apr. 26, 2012

(87) PCT Pub. No.: WO2011/052559
PCT Pub. Date: May 5, 2011

(65) Prior Publication Data
US 2012/0215040 A1  Aug. 23, 2012

(30) Foreign Application Priority Data
Oct. 27, 2009 (JP) ................................ 2009-246633

(51) Int. Cl.
*C07C 17/38* (2006.01)
(52) U.S. Cl.
USPC ....................................................... 570/180
(58) Field of Classification Search
None
See application file for complete search history.

(56) References Cited

U.S. PATENT DOCUMENTS

| | | | |
|---|---|---|---|
| 2,836,622 A | 5/1958 | Tullock | |
| 4,794,204 A | 12/1988 | Post et al. | |
| 5,665,266 A * | 9/1997 | Mahler et al. | 252/67 |
| 6,555,086 B2 | 4/2003 | Ewing et al. | |

FOREIGN PATENT DOCUMENTS

| | | | |
|---|---|---|---|
| EP | 626362 A1 | * | 11/1994 |
| JP | 2001-518869 A | | 10/2001 |
| JP | 2002-047218 A | | 2/2002 |
| JP | 2002047218 A | * | 2/2002 |
| JP | 2003-221213 A | | 8/2003 |
| JP | 2005-154203 A | | 6/2005 |
| JP | 2005-187312 A | | 7/2005 |
| JP | 2009-013101 A | | 1/2009 |

OTHER PUBLICATIONS

English translation of Patent No. JP2002047218A.*
International Search Report of PCT/JP2010/068912, dated Feb. 1, 2011.

* cited by examiner

*Primary Examiner* — Johann R Richter
*Assistant Examiner* — Medhanit Bahta
(74) *Attorney, Agent, or Firm* — Sughrue Mion, PLLC

(57) ABSTRACT

There is provided a fluorine-containing compound purification method for obtaining a high-purity fluorine-containing compound by efficiently separating and removing hydrogen chloride from a fluorine-containing compound that contains hydrogen chloride, i.e., from a crude fluorine-containing compound. The fluorine-containing compound purification method of the present invention comprises the following steps (1) and (2) in this order:

step (1): a step of adding dimethyl ether to a crude fluorine-containing compound that contains a fluorine-containing compound and hydrogen chloride in a molar ratio (dimethyl ether (mol)/hydrogen chloride (mol)) of dimethyl ether to hydrogen chloride being 1.3 or more to prepare a mixture (1) of the crude fluorine-containing compound and dimethyl ether; and step (2): a step of separating and removing a mixture (2) of hydrogen chloride and dimethyl ether from the mixture (1).

6 Claims, No Drawings

FLUORINE-CONTAINING COMPOUND PURIFICATION METHOD

CROSS REFERENCE TO RELATED APPLICATIONS

This application is a National Stage of International Application No. PCT/JP2010/068912 filed Oct. 26, 2010, the contents of which are incorporated herein by reference in their entirety.

TECHNICAL FIELD

The present invention relates to a fluorine-containing compound purification method for separating and removing hydrogen chloride from a fluorine-containing compound that contains hydrogen chloride, i.e., from a crude fluorine-containing compound.

In more detail, the present invention relates to a fluorine-containing compound purification method for efficiently obtaining a high-purity fluorine-containing compound by adding dimethyl ether as a third component to a gaseous or liquid crude fluorine-containing compound that contains hydrogen chloride to prepare a mixture, and separating and removing, from this mixture, a mixture containing hydrogen chloride and dimethyl ether.

BACKGROUND ART

Fluorine-containing compounds are employed for various uses. To be specific, for instance, it is known that fluoromethane ($CH_3F$), trifluoromethane ($CHF_3$) and pentafluoroethane ($CF_3CHF_2$) are used for e.g., refrigerants and material gas for semiconductors, and carbonyl difluoride ($COF_2$) is used for e.g., etching gas for semiconductors and cleaning gas for semiconductors.

To achieve a purity required for these uses, fluorine-containing compound purification methods are known to separate a fluorine-containing compound that contains impurities into a fluorine-containing compound and impurities.

For instance, as a carbonyl difluoride purification method, methods described in the following Patent documents 1 to 3 are known.

Patent document 1 discloses a method for removing silicon tetrafluoride by bringing carbonyl difluoride that contains silicon tetrafluoride as an impurity into contact with a metal fluoride. The silicon tetrafluoride is hardly by-produced in a usual carbonyl difluoride production method.

Patent document 2 discloses a method for separating a mixed gas into carbon dioxide and carbonyl difluoride by introducing the mixed gas that contains carbon dioxide and carbonyl difluoride, each of which has a boiling point close to each other, to a film separation apparatus.

Patent document 3 discloses a method for separating a mixture that contains carbonyl difluoride, obtained through a reaction between an oxygen-containing compound and a fluorine gas, and trifluoromethylhypofluorite as an impurity, into carbonyl difluoride and trifluoromethylhypofluorite by using an activated carbon.

Furthermore, it is also known that a fluorine-containing compound that contains hydrogen chloride as an impurity (a crude fluorine-containing compound), is difficult to separate.

To separate such a crude fluorine-containing compound into a fluorine-containing compound and hydrogen chloride, it has been known to add an aqueous solvent, e.g., an alkali aqueous solution and water, to the crude fluorine-containing compound so as to dissolve hydrogen chloride in the aqueous solvent and thereby separate hydrogen chloride dissolved in the aqueous solvent from the fluorine-containing compound, which does not readily dissolve relatively in the aqueous solvent.

CITATION LIST

Patent Documents

Patent document 1: JP-A-2005-187312
Patent document 2: JP-A-2005-154203
Patent document 3: JP-A-2003-221213

SUMMARY OF THE INVENTION

Problem to be Solved by the Invention

However, the methods using the aqueous solvent as described in Patent documents 1 to 3 cannot be said to be advantageous in terms of separation efficiency. That is, in these methods, when the fluorine-containing compounds are particularly fluoromethane, trifluoromethane and pentafluoroethane, the aqueous solvent dissolves not just hydrogen chloride but also part of the fluorine-containing compound, although the fluorine-containing compound, which is an intended product, does not readily dissolve relatively in the aqueous solvent. This is an economical problem in terms of the dissolution loss of the fluorine-containing compound and the like, and makes it necessary to re-collect the fluorine-containing compound dissolved in the aqueous solvent.

In view of the conventional problem, an object of the present invention is to provide a fluorine-containing compound purification method for obtaining a high-purity fluorine-containing compound by efficiently separating and removing hydrogen chloride from the fluorine-containing compound that contains hydrogen chloride, i.e., from the crude fluorine-containing compound.

Means for Solving the Problem

The present inventors have considered means for separating the crude fluorine-containing compound into a fluorine-containing compound and hydrogen chloride, and have recognized that the purification of the crude fluorine-containing compound that contains hydrogen chloride and a fluorine-containing compound, such as carbonyl difluoride, by distillation operation so as to separate and remove hydrogen chloride from the crude fluorine-containing compound would be extremely difficult for the following reasons (i) and (ii):

(i) The boiling point of the fluorine-containing compound is extremely close to the boiling point of hydrogen chloride; and (ii) When a vapor-liquid equilibrium (x-y line figure) of the fluorine-containing compound and hydrogen chloride is measured, it is found that the fluorine-containing compound and hydrogen chloride have a maximum azeotropic point or a minimum azeotropic point at a specific ratio, or have boiling point curves that are close to each other across a whole region: accordingly, the fluorine-containing compound and hydrogen chloride form an azeotropic mixture or a pseudo azeotropic mixture.

For example, while the boiling point of hydrogen chloride is −85° C., the boiling points of fluoromethane, trifluoromethane and carbonyl difluoride are −78.5° C., −84.4° C. and −85° C., respectively: this shows that the boiling points of the two components are extremely close to each other.

In the case of fluoromethane and trifluoromethane as the fluorine-containing compounds, a maximum azeotropic point exits at hydrogen chloride/fluoromethane=45.7/54.3 (molar ratio), and a minimum azeotropic point exists at hydrogen chloride/trifluoromethane=40.76/59.2 (molar ratio). In the case of carbonyl difluoride as the fluorine-containing compounds, when a vapor-liquid equilibrium of carbonyl difluoride and hydrogen chloride is measured, it is found that carbonyl difluoride and hydrogen chloride have boiling point curves that are close to each other across a whole region, i.e., the relative volatility is 1 or substantially 1. Accordingly, the fluorine-containing compound and hydrogen chloride in the crude fluorine-containing compound form an azeotropic mixture or a pseudo azeotropic mixture, which is a mixture in which when boiling, the liquid phase and the vapor phase have the same composition or substantially the same composition.

The present inventors, seeking to vary the relative volatility, added a third component (entrainer) to the crude fluorine-containing compound to change the vapor-liquid equilibrium relationship from the original relationship, thereby studying the possibility of using extraction distillation to separate the fluorine-containing compound from the crude fluorine-containing compound. As a result, it has been found that when dimethyl ether is added as a third component to the crude fluorine-containing compound, and a vapor-liquid equilibrium of the fluorine-containing compound and dimethyl ether is measured, these two components are not in an azeotropic relationship with each other and thus are separable from each other across a whole region, and on the other hand, when a vapor-liquid equilibrium of hydrogen chloride and dimethyl ether is measured, a maximum azeotropic point exists at dimethyl ether/hydrogen chloride=56/54 (molar ratio).

That is, the fluorine-containing compound and dimethyl ether are not in an azeotropic relationship with each other, while hydrogen chloride and dimethyl ether are in an azeotropic relationship with each other. Accordingly, the crude fluorine-containing compound to which the dimethyl ether has been added is separable into the fluorine-containing compound, and hydrogen chloride and dimethyl ether, by means such as distillation.

Furthermore, the present inventors have studied a molar ratio of dimethyl ether to hydrogen chloride, and have found out that controlling this molar ratio so as to be within a specific range makes it possible to efficiently separate the crude fluorine-containing compound that contains dimethyl ether into hydrogen chloride and a high-purity fluorine-containing compound, and at the same time efficiently collect dimethyl ether having a purity reusable for the purification method of the invention.

The fluorine-containing compound purification method of invention has been completed based on the above findings, and relates to the following [1] to [6].

[1] A fluorine-containing compound purification method comprising the following steps (1) and (2) in this order.

Step (1): a step of adding dimethyl ether to a crude fluorine-containing compound that contains a fluorine-containing compound and hydrogen chloride in a molar ratio (dimethyl ether (mol)/hydrogen chloride (mol)) of dimethyl ether to hydrogen chloride being 1.3 or more to prepare a mixture (1) of the crude fluorine-containing compound and dimethyl ether; and Step (2): a step of separating and removing a mixture (2) of hydrogen chloride and dimethyl ether from the mixture (1).

[2] The fluorine-containing compound purification method as described in [1], wherein the fluorine-containing compound is a fluorinated hydrocarbon having 1 to 3 carbon atoms or a fluorine-containing carbonyl compound having 1 to 3 carbon atoms.

[3] The fluorine-containing compound purification method as described in [1], wherein the fluorine-containing compound is a compound selected from the group consisting of fluoroethane, trifluoroethane, pentafluoroethane and carbonyl difluoride.

[4] The fluorine-containing compound purification method as described in [1], wherein the step (1) and/or the step (2) are carried out at −20° C. to 70° C.

[5] The fluorine-containing compound purification method as described in [1], wherein the step (2) of separating and removing the mixture (2) from the mixture (1) is carried out by distilling the mixture (1).

[6] The fluorine-containing compound purification method as described in [1], wherein the step (1) and the step (2) are repeatedly carried out, the fluorine-containing compound purification method further comprising:

a step (3) of contacting the mixture (2) separated in the step (2) with an alkali aqueous solution and then collecting dimethyl ether, and a step of subjecting the collected dimethyl ether to the step (1).

Effect of the Invention

According to the fluorine-containing compound purification method of the invention, hydrogen chloride is efficiently separated and removed from a fluorine-containing compound that contains hydrogen chloride, i.e., from a crude fluorine-containing compound, thereby obtaining a high purity fluorine-containing compound such as fluoromethane, trifluoromethane, pentafluoroethane and carbonyl difluoride.

EMBODIMENTS FOR CARRYING OUT THE INVENTION

Hereinafter, the fluorine-containing compound purification method of the invention is described in detail.

The fluorine-containing compound purification method of the invention comprises the following steps (1) and (2) in this order:

step (1): a step of adding dimethyl ether to a crude fluorine-containing compound that contains a fluorine-containing compound and hydrogen chloride in a molar ratio (dimethyl ether (mol)/hydrogen chloride (mol)) of dimethyl ether to hydrogen chloride being 1.3 or more to prepare a mixture (1) of the crude fluorine-containing compound and dimethyl ether; and step (2): a step of separating the mixture (1) into a fluorine-containing compound and a mixture (2) of hydrogen chloride and dimethyl ether.

The crude fluorine-containing compound comprises a fluorine-containing compound as an intended product, and hydrogen chloride as an impurity. The crude fluorine-containing compound is obtained, for example, through a reaction between hydrogen fluoride and a chlorine substituted hydrocarbon or a chlorine substituted carbonyl compound (Formulae (1) to (3) described later) or through a reaction between carbon monoxide, chlorine and hydrogen fluoride (Formula (4)).

The crude fluorine-containing compound may be in the form of a gas (a mixed gas) or a liquid (a mixed liquid).

As the fluorine-containing compound contained in the crude fluorine-containing compound, there can be mentioned, for example, a fluorine substituted hydrocarbon (a fluorinated hydrocarbon) and a fluorine substituted carbonyl compound (a fluorine-containing carbonyl compound).

In order to readily exhibit the effect of the invention, the fluorine-containing compound contained in the crude fluorine-containing compound is preferably a fluorinated hydrocarbon having 1 to 3 carbon atoms, or a fluorine-containing carbonyl compound having 1 to 3 carbon atoms, each of which has a boiling point close to the boiling point of hydrogen chloride.

Examples of the fluorinated hydrocarbon or the fluorine-containing carbonyl compound having the above-described number of carbon atoms include fluoromethane ($CH_3F$), trifluoromethane ($CHF_3$), pentafluoroethane ($CF_3CHF_2$), and carbonyl difluoride ($COF_2$).

In the invention, for convenience sake, when the fluorine-containing compounds contained in the crude fluorine-containing compound are fluoromethane, trifluoromethane, pentafluoroethane and carbonyl difluoride, the individual fluorine-containing compounds are referred to as a crude fluoromethane, a crude trifluoromethane, a crude pentafluoroethane, and a crude carbonyl difluoride, respectively.

The crude fluoromethane is obtained, for example, by reacting chloromethane with hydrogen fluoride (Formula 1) in the presence of a fluorination catalyst at a gas phase state.

$$CH_3Cl + HF \rightarrow CH_3F + HCl \qquad \text{(Formula 1)}$$

The crude trifluoromethane is obtained, for example, by reacting trichloromethane with hydrogen fluoride (Formula 2) in the presence of a fluorination catalyst at a gas phase state.

$$CHCl_3 + 3HF \rightarrow CHF_3 + 3HCl \qquad \text{(Formula 2)}$$

The crude carbonyl difluoride is obtained, for example, by reacting hydrogen fluoride with phosgene (Formula 3), or by reacting hydrogen fluoride with carbon monoxide, chlorine and hydrogen fluoride (Formula 4), in the presence of a fluorination catalyst at a gas phase state.

$$COCl_2 + 2HF \rightarrow COF_2 + 2HCl \qquad \text{(Formula 3)}$$

$$CO + Cl_2 + 2HF \rightarrow COF_2 + 2HCl \qquad \text{(Formula 4)}$$

In the invention, in the step (1), dimethyl ether is added to the crude fluorine-containing compound in a molar ratio (dimethyl ether (mol)/hydrogen chloride (mol)) of dimethyl ether to hydrogen chloride being 1.3 or more to prepare a mixture (1) of the crude fluorine-containing compound and dimethyl ether. As described previously, dimethyl ether and hydrogen chloride have a maximum azeotropic point at dimethyl ether/hydrogen chloride=56/44 (molar ratio), and at 30° C., have an azeotropic composition at dimethyl ether/hydrogen chloride being 1.3. Accordingly, the molar ratio of dimethyl ether to hydrogen chloride being less than 1.3 results in insufficient formation of an azeotropic mixture of hydrogen chloride and dimethyl ether, and prevents efficient separation of a high-purity fluorine-containing compound from the mixture of hydrogen chloride and dimethyl ether, and furthermore, causes the reaction of dimethyl ether with hydrogen chloride to by-produce a large amount of methyl chloride and the like.

The above molar ratio is preferably 1.3 to 8.0, more preferably 1.5 to 5.0.

A larger ratio of dimethyl ether by-produces a less amount of methyl chloride, but may require a large scale of equipment for collecting and treating dimethyl ether.

The step (1) and/or the step (2) are carried out preferably at −20 to 70° C., more preferably 0 to 50° C. If the temperature at which the step (1) and/or the step (2) are carried out is not higher than −20° C., the amount of methyl chloride by-produced can be advantageously decreased, but equipment for e.g., cooling may be required. On the other hand, if the temperature at which the step (1) and/or the step (2) are carried out is not lower than 70° C., a by-product such as methyl chloride may be increased.

The methyl chloride is not under an azeotropic relationship with the fluorine-containing compound, judging from the previously described vapor-liquid equilibrium measurement, and thus methyl chloride is separable from the fluorine-containing compound across a whole region.

The pressure in the step (2) varies depending on an addition amount of dimethyl ether, a temperature of the mixture (1) and the like, but is usually 0.3 to 1.0 MPa, preferably 0.5 to 0.9 MPa. Such pressure condition can reduce the cost associated with equipment, e.g., cooling equipment and pressure resistant equipment, and thus favorable in terms of economical viewpoint.

If the crude fluorine-containing compound contains an excessive amount of impurities (a total of hydrogen chloride and impurities other than hydrogen chloride (e.g., unreacted products and by-products)), prior to the step (1), the content of the impurities contained in the crude fluorine-containing compound may be decreased, for example, by separation means, e.g., distillation. Decreasing the content of the impurities contained in the crude fluorine-containing compound can alleviate energy burden at the hydrogen chloride separation step.

The fluorine-containing compound purification method of the invention comprises a step of separating and removing a mixture (2) of hydrogen chloride and dimethyl ether from the mixture (1) of the crude fluorine-containing compound and dimethyl ether prepared in the step (1). The mixture (2) of hydrogen chloride and dimethyl ether as used herein is a mixture containing hydrogen chloride and dimethyl ether, but occasionally contains a trace amount of a fluorine-containing compound that was not separated and removed completely in the step (2).

As means for separating and removing the mixture (2) from the mixture (1) in the step (2), there can be mentioned, for example, distillation, decantation and other separation means. In terms of efficiency and scale increase, a preferred separation means is distillation.

In the case of the crude fluoromethane, the crude trifluoromethane, the crude pentafluoroethane and the crude carbonyl difluoride as the crude fluorine-containing compounds, distilling the mixture (1) results in collecting the fluorine-containing compound, which is a low boiling component, from a column top as a column top component, and on the other hand collecting the mixture (2) of dimethyl ether and hydrogen chloride, which is a high boiling component, from a column bottom as a column bottom component.

If the distillation apparatus has plural distillation columns, the fluorine-containing compound may be collected at a first distillation column, and the fluorine-containing compound thus collected may be subjected to distillation operation at a second distillation column.

Furthermore, in order to obtain a fluorine-containing compound with higher purity, the fluorine-containing compound obtained in the step (2) may be subjected to a purification step such as precision distillation. Through such a precision distillation step, a low boiling component such as an inert (an inert component) contained in the fluorine-containing compound can be removed.

Moreover, in order to obtain a fluorine-containing compound with much higher purity, the fluorine-containing compound from which the low boiling component has been removed through the purification step may be contacted with an adsorbent, e.g., molecular sieving carbon, thereby removing a trace amount of hydrogen fluoride and the like contained in the fluorine-containing compound.

Furthermore, it is favorable to collect dimethyl ether having a purity reusable for the purification method of the invention and repeatedly use (reuse) dimethyl ether from a economical view, the purification method may be such that the step (1) and the step (2) are repeatedly carried out, and a step (3) of contacting the mixture (2) separated in the step (2) with an alkali aqueous solution and then collecting dimethyl ether and a step of subjecting the dimethyl ether collected to the step (1) are further included.

As the alkali aqueous solution used herein, there can be mentioned, for example, an aqueous solution of sodium hydroxide and an aqueous solution of potassium hydroxide.

The temperature at which the contacting with the alkali aqueous solution is preferably a low temperature, more preferably not higher than 40° C., in order to reduce the dissolution loss of dimethyl ether in the aqueous solution.

The mixture (2) to which the alkali aqueous solution has been added, is separated, by means such as distillation, into hydrogen chloride and water, and dimethyl ether. Thereby, dimethyl ether is collected. Furthermore, according to necessity, it is desirable that the dimethyl ether collected is contacted with a dehydrating agent so as to remove a water content contained in a slight amount in dimethyl ether. A preferred example of the dehydrating agent is a zeolite, with specific examples of such a zeolite including molecular sieves 3A, 4A and 5A.

EXAMPLES

Hereinafter, the fluorine-containing compound purification method of the invention is described with reference to Examples, but the invention is in no way limited to these Examples.

[Preparation of Fluorination Catalyst]
[Catalyst (1)]

8.2 g of chromium chloride ($CrCl_3 \cdot 6H_2O$) was dissolved in 52 mL of pure water to prepare a catalyst solution. Then, in this catalyst solution, 100 mL of a spherical high-purity activated alumina (NST-3, manufactured by Nikki-Universal Co., Ltd.) was soaked, thereby having the alumina absorb a whole amount of the catalyst solution.

The alumina absorbing the catalyst solution was dried and exsiccated over a hot water bath at 90° C., and dried in an air circulating type heated air drier at 110° C. for 10 hours, thereby obtaining a dried catalyst. Further, the dried catalyst was packed into a glass calcining tube, into which air was flown at a space velocity ($SV_o$) of 500 $Hr^{-1}$. The temperature was increased to 400° C., and calcining was carried out for 8 hours. Thereby, a catalyst (1) was obtained.

Then, 70 mL of the catalyst (1) obtained was packed into an Inconel (trade mark) 600 reaction vessel with an inner diameter of 1 inch and a length of 1 m.

Then, the catalyst (1) was subjected to partial fluorination treatment using a hydrogen fluoride gas diluted with nitrogen and 100% by volume of hydrogen fluoride under the following conditions, thereby activating the catalyst (1) to obtain an activated catalyst (1).

[Conditions of Partial Fluorination Treatment]
Concentration of hydrogen fluoride: 25 to 100% by volume
Treatment temperature: 150 to 350° C.
Treatment time: about 10 hours Example 1

While a nitrogen gas was flown into the reaction vessel to which 70 mL of the activated catalyst (1) had been charged, the temperature in the reaction vessel was kept at 250° C. Then, while 100 mL/min of hydrogen fluoride was flown, and further 60 mL/min of chloromethane was flown, the supply of the nitrogen gas was terminated, and reaction (synthesis reaction) was started.

Four hours after the start of the reaction, an exit gas containing $CH_3F$ and by-products was collected from an exit valve of the reaction vessel into a first SUS cylinder (volume: 1000 mL). Then, the exit gas collected was cooled and liquefied to obtain 450 g of a mixture A. Moreover, the exit gas was collected into a second SUS cylinder (volume: 500 mL) and cooled to obtain 150 g of a mixture A.

The mixture A collected into the second SUS cylinder was analyzed by FT-IR (cell: $CaF_2$). The result is shown as below.
[FT-IR Analysis Result of Mixture A]
$CH_3F$ 44.64% by mass
HCl 47.93% by mass
HF 2.45% by mass
$CH_3Cl$ 4.90% by mass
Others 0.08% by mass The mixture A was subjected to distillation separation under the following conditions, and separated into a component at a distillation column top (mixture A': 120 g) and a liquid component at a column bottom. The mixture A' was analyzed by FT-IR (cell: $CaF_2$). The result is shown as below.
(Conditions of Distillation of Mixture A)
Distillation scale: charged amount of the mixture A: 150 g
Distillation column: a packing column: 16 mm×500 mm
Packed substance: about 100 mL of HELI PACK No. 2 (manufactured by TO-TOKU Engineering Corporation)
Number of theoretical stages: 15 stages
Operation Conditions
 Pressure: about 0.8 MPa
 Oil bath temperature (distillation temperature): 36 to 45° C.
 Reflux ratio: 15
(Analysis Result of Column Top Distillate Component (Mixture A')
$CH_3F$ 48.18% by mass
HCl 51.73% by mass
Others 0.09% by mass About 170 g (3.69 mol) of dimethyl ether was added to 120 g of the mixture A' obtained to prepare a mixture B (dimethyl ether/HCl (molar ratio)=2.34). Further, the mixture B was distilled under the following conditions, and was separated into a column top distillate component and a column bottom liquid component. Then, the column top distillate component was analyzed by FT-IR (cell: $CaF_2$). In addition, the amount of the decomposition of dimethyl ether in the column bottom liquid component was analyzed by FT-IR (cell: $CaF_2$). The result is shown as below.
(Conditions of Distillation of Mixture B)
Distillation scale: charged amount of the mixture B: about 285 g
Distillation column: a packing column: 16 mm×500 mm
Packed substance: about 100 mL of HELI PACK No. 2 (manufactured by TO-TOKU Engineering Corporation)
Number of theoretical stages: 15 stages
Operation Conditions
 Pressure: about 0.8 MPa
 Oil bath temperature (distillation temperature): 35° C.
 Reflux ratio: 15
(Analysis Result of Column Top Distillate Component)
 $CH_3F$ 99.90% by mass
 Other components 0.10% by mass
(Analysis Result of Column Bottom Liquid Component)
 Decomposition amount of dimethyl ether: 1.30% by mol Other components as described above were mainly oxygen, nitrogen and a carbon dioxide gas.

As is clear from the analysis result of the column top distillate component, the distillation of the mixture B prepared by adding dimethyl ether to the mixture A' in a molar ratio of dimethyl ether to HCl being 2.34 resulted in obtaining a high-purity $CH_3F$. The decomposition amount of dimethyl ether was 1.30% by mol, and thus a small decomposition amount.

Example 2

While a nitrogen gas was flown into the reactor vessel to which 50 mL of the activated catalyst (1) had been charged, the temperature was kept at 165° C. Then, while 162 mL/min of a hydrogen fluoride gas was flown, and further 57 mL/min of phosgene was flown, the supply of the nitrogen gas was terminated, and reaction (synthesis reaction) was started.

Four hours after the start of the reaction, an exit gas containing carbonyl difluoride and by-products was collected from an exit valve of the reaction vessel into a SUS cylinder (volume: 500 mL).

Then, the exit gas collected was cooled to obtain 200 g of a mixture A. The mixture A was analyzed by FT-IR (cell: $CaF_2$). The result is shown as below.
[FT-IR Analysis Result of Mixture A]
$COF_2$ 41.4% by mass
HCl 46.7% by mass
HF 11.7% by mass
Others 0.2% by mass The mixture A was subjected to distillation separation under the following conditions, and separated into a column top distillate component (mixture A': 170 g) and a column bottom liquid component. The mixture A' was analyzed by FT-IR (cell: $CaF_2$). The result is shown as below.
(Conditions of Distillation of Mixture A)
Distillation scale: charged amount of the mixture A: 200 g
Distillation column: a packing column: 16 mm×500 mm
Packed substance: about 100 mL of HELI PACK No. 2 (manufactured by TO-TOKU Engineering Corporation)
Number of theoretical stages: 15 stages
Operation Conditions
　Pressure: about 0.8 MPa
　Oil bath temperature (distillation temperature): 36 to 45° C.
　Reflux ratio: 15
(Analysis Result of Column Top Distillate Component (Mixture A')
$COF_2$ 46.99% by mass
HCl 53.01% by mass
$HCl/COF_2$=2.47 mol/1.21 mol (=2.04) (molar ratio)

Then, under the condition of a temperature of 35° C., about 170 g (3.69 mol) of dimethyl ether was added to 170 g of the mixture A' collected, to prepare a mixture B (dimethyl ether/HCl (molar ratio)=3.69/2.47=1.50). The mixture B was distilled under the following conditions, and was separated into a column top distillate component and a column bottom liquid component. Then, the column top distillate component was analyzed by FT-IR (cell: $CaF_2$). In addition, the amount of the decomposition of dimethyl ether in the column bottom liquid component was analyzed by FT-IR (cell: $CaF_2$). The result is shown as below.
(Conditions of Distillation of Mixture B)
Distillation scale: charged amount of the mixture B: about 335 g
Distillation column: a packing column: 16 mm×500 mm
Packed substance: about 100 mL of HELI PACK No. 2 (manufactured by TO-TOKU Engineering Corporation)
Number of theoretical stages: 15 stages
Operation Conditions
　Pressure: about 0.8 MPa
　Oil bath temperature (distillation temperature): 35° C.
　Reflux ratio: 15
(Analysis Result of Column Top Distillate Component)
　$COF_2$ 98.98% by mass
　Other components 1.02% by mass
　Other components as described above were mainly oxygen, nitrogen and a carbon dioxide gas.
(Analysis Result of Column Bottom Liquid Component)
　Decomposition amount of dimethyl ether: 1.29% by mol As is clear from the analysis result of the column top distillate component, the distillation of the mixture B prepared by adding dimethyl ether to the mixture A' in a molar ratio of dimethyl ether to HCl being 1.50 resulted in obtaining a high-purity $COF_2$.

The decomposition amount of dimethyl ether was 1.29% by mol, and thus a small decomposition amount.

Comparative Example 1

The synthesis reaction of Example 2 was carried out for about four hours, and an exit gas containing carbonyl difluoride and by-products was collected into a SUS cylinder (volume: 500 mL). Then, the exit gas collected was cooled to obtain 170 g of a mixture A. The mixture A was analyzed by FT-IR (cell: $CaF_2$). The result is shown as below.
$COF_2$ 41.1% by mass
HCl 46.5% by mass
HF 12.1% by mass
Others 0.3% by mass The mixture A was distilled under the following conditions, and separated into a column top distillate component and a column bottom liquid component. The column top distillate component (mixture A') was analyzed by FT-IR (cell: $CaF_2$). The result is shown as below.
(Conditions of Distillation of Mixture A)
Distillation scale: charged amount of the mixture A: 170 g
Distillation column: a packing column: 16 mm×500 mm
Packed substance: about 100 mL of HELI PACK No. 2 (manufactured by TO-TOKU Engineering Corporation)
Number of theoretical stages: 15 stages
Operation Conditions
　Pressure: about 0.8 MPa
　Oil bath temperature (distillation temperature): 36 to 45° C.
　Reflux ratio: 15
(Analysis Result of Column Top Distillate Component)
$COF_2$ 46.9% by mass
HCl 53.1% by mass
$HCl/COF_2$ (molar ratio) was 2.04 mol/0.995 mol (=2.05).

Then, under the condition of a temperature of 35° C., about 94 g (2.04 mol) of dimethyl ether was added to 140 g of the mixture A' collected, to prepare about 225 g of a mixture B (dimethyl ether/HCl (molar ratio)=1.0).

The mixture B was distilled under the same conditions as in the distillation of the mixture B in Example 2, and was separated into a column top distillate component and a column bottom liquid component. Then, the column top distillate component was analyzed by FT-IR (cell: $CaF_2$). The amount of the decomposition of dimethyl ether was analyzed by FT-IR (cell: $CaF_2$). The result is shown as below. In the mixture B, dimethyl ether/HCl/$COF_2$ (molar ratio) was 2.04/2.04/0.995.

(Analysis Result of Column Top Distillate Component)
    $COF_2$ 89.13% by mass
    HCl 10.67% by mass
    Other components 0.20% by mass
    Other components as described above were mainly oxygen, nitrogen and a carbon dioxide gas.
(Analysis Result of Column Bottom Liquid Component)
    Decomposition amount of dimethyl ether: 3.70% by mol
    As is clear from the analysis result of the column top distillate component, the distillation of the mixture B prepared by adding dimethyl ether to the mixture A' in a molar ratio of dimethyl ether to HCl being 1.0 failed to obtain a high-purity $COF_2$. The decomposition amount of dimethyl ether was 3.70% by mol, and the loss amount of dimethyl ether and the increase of $CH_3Cl$, which was an impurity, were considerable.

Example 3

The synthesis reaction of Example 2 was carried out for about four hours, and an exit gas containing carbonyl difluoride and by-products was collected into a SUS cylinder (volume: 500 mL). Then, the exit gas collected was cooled to obtain about 130 g of a mixture A. The mixture A was analyzed by FT-IR (cell: $CaF_2$). The result is shown as below.
$COF_2$ 41.2% by mass
HCl 46.3% by mass
HF 12.3% by mass
Others 0.2% by mass
    The mixture A was distilled under the following conditions, and separated into about 100 g of a column top distillate component (mixture A') and a column bottom liquid component. The column top distillate component (mixture A') was analyzed by FT-IR (cell: $CaF_2$). The result is shown as below.
(Conditions of Distillation of Mixture A)
Distillation scale: charged amount of the mixture A: 130 g
Distillation column: a packing column: 16 mm×500 mm
Packed substance: about 100 mL of HELI PACK No. 2 (manufactured by TO-TOKU Engineering Corporation)
Number of theoretical stages: 15 stages
Operation Conditions
    Pressure: about 0.8 MPa
    Oil bath temperature (distillation temperature): 36 to 45° C.
    Reflux ratio: 15
(Analysis Result of Column Top Distillate Component)
$COF_2$ 46.9% by mass
HCl 53.1% by mass
$HCl/COF_2$ (molar ratio) was 1.45 mol/0.71 mol (=2.04).
    Then, about 336 g (about 7.29 mol) of dimethyl ether was added to 100 g of the mixture A', which was the column top distillate component, to prepare about 436 g of a mixture B (dimethyl ether/HCl (molar ratio)=5.0). The mixture B was distilled under the same conditions as in the distillation of the mixture B in Example 2, and was separated into a column top distillate component and a column bottom liquid component. Then, the column top distillate component was analyzed by FT-IR (cell: $CaF_2$). Further, the amount of the decomposition of dimethyl ether was analyzed by FT-IR (cell: $CaF_2$). The result is shown as below.
    In the mixture B, dimethyl ether/HCl/$COF_2$ (molar ratio) was 7.29/1.45/0.71.
(Analysis Result of Column Top Distillate Component)
    $COF_2$ 99.02% by mass
    Other components 0.98% by mass
    Other components as described above were mainly oxygen, nitrogen and a carbon dioxide gas.
(Analysis Result of Column Bottom Liquid Component)
    Decomposition amount of dimethyl ether: 0.05% by mol
    As is clear from the analysis result of the column top distillate component, the distillation of the mixture B prepared by adding dimethyl ether to the mixture A' in a molar ratio of dimethyl ether to HCl being 5.0 resulted in obtaining a high-purity $COF_2$. The decomposition amount of dimethyl ether was 0.05% by mol, and thus a small decomposition amount.

The invention claimed is:
1. A fluorine-containing compound purification method comprising the following steps (1) and (2) in this order:
    step (1): a step of adding dimethyl ether to a crude fluorine-containing compound that contains a fluorine-containing compound and hydrogen chloride in a molar ratio (dimethyl ether (mol)/hydrogen chloride (mol)) of dimethyl ether to hydrogen chloride being 1.3 or more to prepare a mixture (1) of the crude fluorine-containing compound and dimethyl ether; and
    step (2): a step of separating and removing a mixture (2) of hydrogen chloride and dimethyl ether from the mixture (1).
2. The fluorine-containing compound purification method according to claim 1, wherein the fluorine-containing compound is a fluorinated hydrocarbon having 1 to 3 carbon atoms or a fluorine-containing carbonyl compound having 1 to 3 carbon atoms.
3. The fluorine-containing compound purification method according to claim 1, wherein the fluorine-containing compound is a compound selected from the group consisting of fluoroethane, trifluoroethane, pentafluoroethane and carbonyl difluoride.
4. The fluorine-containing compound purification method according to claim 1, wherein the step (1) and/or the step (2) are carried out at −20° C. to 70° C.
5. The fluorine-containing compound purification method according to claim 1, wherein the step (2) of separating and removing the mixture (2) from the mixture (1) is carried out by distilling the mixture (1).
6. The fluorine-containing compound purification method according to claim 1, wherein the step (1) and the step (2) are repeatedly carried out, the fluorine-containing compound purification method further comprising:
    a step (3) of contacting the mixture (2) separated in the step (2) with an alkali aqueous solution and then collecting dimethyl ether, and
    a step of subjecting the collected dimethyl ether to the step (1).

* * * * *